(12) United States Patent
Norris et al.

(10) Patent No.: US 8,452,383 B2
(45) Date of Patent: May 28, 2013

(54) TEMPERATURE PROFILE MAPPING AND GUIDED THERMOTHERAPY

(75) Inventors: Peter E. Norris, Cambridge, MA (US); Xiao-Li Li, Lexington, MA (US); Andrey Vertikov, Westwood, MA (US)

(73) Assignee: Tomophase Corporation, Burlington, MA (US)

( * ) Notice: Subject to any disclaimer, the term of this patent is extended or adjusted under 35 U.S.C. 154(b) by 84 days.

(21) Appl. No.: 12/920,309

(22) PCT Filed: Mar. 2, 2009

(86) PCT No.: PCT/US2009/035773
§ 371 (c)(1),
(2), (4) Date: Nov. 29, 2010

(87) PCT Pub. No.: WO2009/108950
PCT Pub. Date: Sep. 3, 2009

(65) Prior Publication Data
US 2011/0066035 A1    Mar. 17, 2011

Related U.S. Application Data

(60) Provisional application No. 61/032,853, filed on Feb. 29, 2008.

(51) Int. Cl.
*A61B 6/00* (2006.01)
(52) U.S. Cl.
USPC .............. 600/478; 600/476; 600/473; 606/46

(58) Field of Classification Search
USPC .............................. 600/473–480; 606/41–52
See application file for complete search history.

(56) References Cited

U.S. PATENT DOCUMENTS

| | | | |
|---|---|---|---|
| 4,402,311 A | 9/1983 | Hattori | |
| 4,848,867 A | 7/1989 | Kajioka et al. | |
| 4,878,492 A | 11/1989 | Sinofsky et al. | |
| 4,991,938 A | 2/1991 | Buhrer et al. | |
| 5,088,493 A | 2/1992 | Giannini et al. | |
| 5,202,745 A | 4/1993 | Sorin et al. | |
| 5,321,501 A * | 6/1994 | Swanson et al. | 356/479 |
| 5,459,570 A | 10/1995 | Swanson et al. | |
| 5,659,392 A | 8/1997 | Marcus et al. | |
| 5,710,630 A | 1/1998 | Essenpreis et al. | |
| 5,784,162 A | 7/1998 | Cabib et al. | |

(Continued)

FOREIGN PATENT DOCUMENTS

| CN | 2524241 | 12/2002 |
|---|---|---|
| EP | 0 429 297 | 5/1991 |

(Continued)

OTHER PUBLICATIONS

International Search Report and Written Opinion dated Apr. 28, 2011 for International Application No. PCT/US2010/046874, filed Aug. 26, 2010 (6 pages).

(Continued)

*Primary Examiner* — Sanjay Cattungal
(74) *Attorney, Agent, or Firm* — Perkins Coie LLP

(57) ABSTRACT

Techniques, apparatus and systems that use an optical probe head to deliver light to a target and to collect light from the target for imaging and monitoring a target while a separate radiation is applied to treat the target.

15 Claims, 10 Drawing Sheets

U.S. PATENT DOCUMENTS

| | | | |
|---|---|---|---|
| 5,803,909 A | 9/1998 | Maki et al. | |
| 5,912,762 A | 6/1999 | Li et al. | |
| 6,034,774 A | 3/2000 | Marcus et al. | |
| 6,134,003 A * | 10/2000 | Tearney et al. | 356/479 |
| 6,201,989 B1 | 3/2001 | Whitehead et al. | |
| 6,219,565 B1 | 4/2001 | Cupp et al. | |
| 6,246,818 B1 | 6/2001 | Fukushima | |
| 6,252,666 B1 | 6/2001 | Mandella et al. | |
| 6,282,011 B1 * | 8/2001 | Tearney et al. | 359/287 |
| 6,377,840 B1 | 4/2002 | Gritsenko et al. | |
| 6,421,164 B2 * | 7/2002 | Tearney et al. | 359/287 |
| 6,451,009 B1 | 9/2002 | Dasilva et al. | |
| 6,485,413 B1 * | 11/2002 | Boppart et al. | 600/160 |
| 6,498,942 B1 | 12/2002 | Esenaliev et al. | |
| 6,501,551 B1 * | 12/2002 | Tearney et al. | 356/477 |
| 6,522,407 B2 | 2/2003 | Everett et al. | |
| 6,549,801 B1 | 4/2003 | Chen et al. | |
| 6,585,639 B1 | 7/2003 | Kotmel et al. | |
| 6,608,717 B1 | 8/2003 | Medford et al. | |
| 6,609,425 B2 | 8/2003 | Ogawa | |
| 6,615,072 B1 | 9/2003 | Izatt et al. | |
| 6,687,010 B1 | 2/2004 | Horii et al. | |
| 6,709,402 B2 | 3/2004 | Dekker | |
| 6,725,073 B1 | 4/2004 | Motamedi et al. | |
| 6,738,144 B1 | 5/2004 | Dogariu | |
| 6,753,966 B2 | 6/2004 | Von Rosenberg | |
| 6,847,453 B2 | 1/2005 | Bush | |
| 6,891,984 B2 | 5/2005 | Petersen et al. | |
| 6,901,284 B1 | 5/2005 | Maki et al. | |
| 6,903,820 B2 | 6/2005 | Wang | |
| 6,903,854 B2 | 6/2005 | Gelikonov et al. | |
| 6,943,881 B2 | 9/2005 | Wang | |
| 7,023,563 B2 | 4/2006 | Li | |
| 7,039,454 B1 | 5/2006 | Kaga et al. | |
| 7,058,155 B2 | 6/2006 | Piacsek et al. | |
| 7,170,574 B2 | 1/2007 | Tan et al. | |
| 7,207,984 B2 | 4/2007 | Farr et al. | |
| 7,254,429 B2 | 8/2007 | Schurman et al. | |
| 7,259,851 B2 | 8/2007 | Wang | |
| 7,263,394 B2 | 8/2007 | Wang | |
| 7,428,053 B2 | 9/2008 | Feldchtein et al. | |
| 7,456,965 B2 | 11/2008 | Wang | |
| 7,595,879 B2 | 9/2009 | Wang | |
| 7,706,646 B2 | 4/2010 | Wang et al. | |
| 7,831,298 B1 * | 11/2010 | Wang et al. | 600/473 |
| 8,041,162 B2 | 10/2011 | Wang et al. | |
| 2002/0049370 A1 | 4/2002 | Laufer et al. | |
| 2002/0126347 A1 | 9/2002 | Hogan | |
| 2002/0131049 A1 | 9/2002 | Schmitt | |
| 2003/0020920 A1 | 1/2003 | Dave et al. | |
| 2003/0114878 A1 | 6/2003 | Diederich et al. | |
| 2003/0137669 A1 | 7/2003 | Rollins et al. | |
| 2003/0187319 A1 | 10/2003 | Kaneko et al. | |
| 2004/0001716 A1 | 1/2004 | Daou et al. | |
| 2004/0140425 A1 | 7/2004 | Iizuka et al. | |
| 2004/0218845 A1 | 11/2004 | Li et al. | |
| 2004/0246490 A1 | 12/2004 | Wang | |
| 2004/0247268 A1 | 12/2004 | Ishihara et al. | |
| 2004/0258377 A1 | 12/2004 | Berkey et al. | |
| 2004/0260158 A1 | 12/2004 | Hogan | |
| 2005/0018202 A1 | 1/2005 | Wang | |
| 2005/0053109 A1 | 3/2005 | Hogan | |
| 2005/0075547 A1 | 4/2005 | Wang | |
| 2005/0286055 A1 | 12/2005 | Wang | |
| 2006/0079762 A1 | 4/2006 | Norris et al. | |
| 2006/0089548 A1 | 4/2006 | Hogan | |
| 2006/0100490 A1 | 5/2006 | Wang et al. | |
| 2007/0103683 A1 | 5/2007 | Wang | |
| 2007/0115476 A1 | 5/2007 | Feldchtein et al. | |
| 2008/0030740 A1 | 2/2008 | Wang | |
| 2008/0033300 A1 | 2/2008 | Hoang et al. | |
| 2008/0119701 A1 | 5/2008 | Milner et al. | |
| 2008/0267562 A1 | 10/2008 | Wang et al. | |
| 2009/0073444 A1 | 3/2009 | Wang | |
| 2010/0014093 A1 | 1/2010 | Wang | |
| 2010/0091282 A1 | 4/2010 | Wang | |
| 2010/0201985 A1 | 8/2010 | Wang et al. | |
| 2011/0029049 A1 | 2/2011 | Vertikov et al. | |
| 2011/0285996 A1 | 11/2011 | Wang | |
| 2012/0033911 A1 | 2/2012 | Wang et al. | |

FOREIGN PATENT DOCUMENTS

| | | |
|---|---|---|
| EP | 0 527 050 | 2/1993 |
| JP | 2001-066245 | 3/2001 |
| JP | 2002-013907 | 1/2002 |
| JP | 2004-317437 | 11/2004 |
| WO | 03/062802 | 7/2003 |
| WO | 2005/001522 | 1/2005 |
| WO | 2006/041997 | 4/2006 |
| WO | 2006/045013 | 4/2006 |
| WO | 2008/134449 | 11/2008 |

OTHER PUBLICATIONS

El-Tonsy, M.H., et al., "Continuous-wave Nd:Yag laser hyperthermia: a successful modality in treatment of basal cell carcinoma," Dermatology Online Journal, 10(2):12 pages, Oct. 2004.

European Search Report dated Nov. 18, 2010 for European Patent Application No. 05813935.3, filed Oct. 20, 2005 (9 pages).

European Search Report dated Nov. 2, 2010 for European Patent Application No. 04754292.3, filed Jun. 4, 2004 (4 pages).

Goldberg, S.N., et al., "Thermal ablation therapy for focal malignancy: a unified approach to underlying principles, techniques, and diagnostic imaging guidance," AJR American Journal Roentgenology, 174(2):323-331, Feb. 2000.

Handbook of Optics, 2nd Edition, vol. 1: Fundamentals, Techniques, & Design, Optical Society of America, McGraw-Hill Professional, pp. 42.68-42.73, Sep. 1994.

International Preliminary Report on Patentability dated Dec. 22, 2005 for International Application No. PCT/US04/17649, filed Jun. 4, 2004 (7 pages).

International Preliminary Report on Patentability dated Feb. 24, 2009 for International Application No. PCT/US05/35951, filed Oct. 5, 2005 (9 pages).

International Preliminary Report on Patentability dated Nov. 5, 2009 for International Application No. PCT/US2008/061451, filed Apr. 24, 2008 (6 pages).

International Search Report and Written Opinion dated Aug. 29, 2008 for International Application No. PCT/US05/35951, filed Oct. 5, 2005 (10 pages).

International Search Report and Written Opinion dated Nov. 20, 2009 for International Application No. PCT/US2009/035773, filed Mar. 2, 2009 (7 pages).

International Search Report and Written Opinion dated Oct. 17, 2008 for International Application No. PCT/US2008/061451, filed Apr. 24, 2008 (7 pages).

International Search Report and Written Opinion dated Oct. 4, 2007 for International Application No. PCT/US05/37730, filed Oct. 20, 2005 (5 pages).

James, A., et al., "Airway smooth muscle in health and disease; methods of measurement and relation to function," The European Respiratory Journal, 15(4):782-789, Apr. 2000.

Lucroy, M.D., et al., "Selective laser-induced hyperthermia for the treatment of spontaneous tumors in dogs," Journal of X-Ray Science and Technology, 10(3-4):237-243, (2002).

Miller, J.D., et al., "A Prospective Feasibility Study of Bronchial Thermoplasty in the Human Airway," Chest, 127 (6):1999-2006, Jun. 2005.

Nikfarjam, M., et al., "Interstitial laser thermotherapy for liver tumours," British Journal of Surgery, 90(9):1033-1047, Sep. 2003.

Office Action dated Feb. 12, 2010 for Chinese Patent Application No. 200580043930.4 (12 pages).

Office Action dated Mar. 17, 2010 for Japanese Patent Application No. 2006-515173 (4 pages).

Office Action dated Nov. 20, 2009 for Chinese Patent Application No. 200480021343.0 (25 pages).

Office Action dated Oct. 22, 2010 for Canadian Patent Application No. 2,528,417 (3 pages).

Tearney, G., et al., "In Vivo Endoscopic Optical Biopsy with Optical Coherence Tomography," Science, 276 (5321):2037-2039, Jun. 1997.

Tumlinson, A., et al., "Endoscope-tip interferometer for ultrahigh resolution frequency domain optical coherence tomography in mouse colon," Optics Express, 14(5):1878-1887, Mar. 2006.

Vakhtin, A.B., et al., "Common-Path Interferometer for Frequency-Domain Optical Coherence Tomography," Applied Optics, 42(34):6953-6958, Dec. 2003.

Yun, S., et al., "Comprehensive volumetric optical microscopy in vivo," Nature Medicine, 12(12):1429-1433, Nov. 2006.

Ziemann, V., et al., "Ideas for an interferometric thermometer," Nuclear Instruments and Methods in Physics Research Section A: Accelerators, Spectrometers, Detectors and Associated Equipment, 564(1):587-589, Aug. 2006.

An, L., et al., "In vivo volumetric imaging of vascular perfusion within human retina and choroids with optical micro-angiography," Optics Express, 16(15):11438-11452, Jul. 2008.

Mariampillai, A., et al., "Doppler optical cardiogram gated 2D color flow imaging at 1000 fps and 4D in vivo visualization of embryonic heart at 45 fps on a swept source OCT system," Optics Express, 15(4):1627-1638, Feb. 2007.

Yang, V., et al., "High speed, wide velocity dynamic range Doppler optical coherence tomography (Part I): System design, signal processing, and performance," Optics Express, 11(7):794-809, Apr. 2003.

* cited by examiner

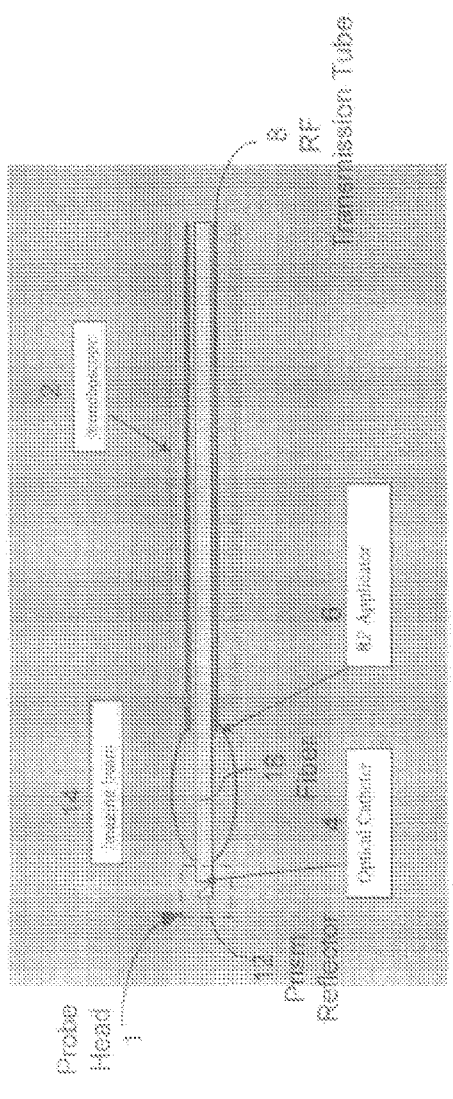
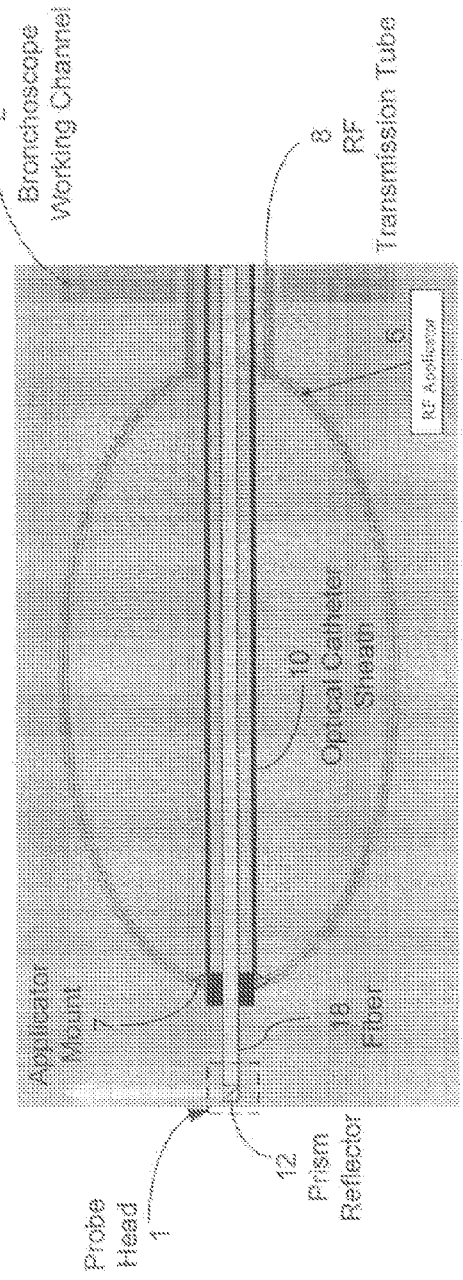
FIG. 1A
FIG. 1B

TEMPERATURE PROFILE MAPPING AND GUIDED THERMOTHERAPY

PRIORITY CLAIM

This patent document claims the priority of U.S. Provisional Application No. 61/032,853 entitled "Temperature Profile Mapping with Tomophase OCT Apparatus" and filed on Feb. 29, 2008, the entire disclosure of which is incorporated by reference as part of the disclosure of this document.

BACKGROUND

This application relates to techniques, apparatus and systems that use optical waveguides to deliver light to a targeted area for optical detection of tissues, organs and other objects in medical, biological and other applications.

Light can be guided through a light pipe or optical waveguide such as optic fiber to a target to obtain optical images, optical measurements and other operations of the target. The optical waveguide such as optic fiber can be used to reach the target at a location that is otherwise difficult to reach or requires some preparatory procedures to make the target more accessible. For example, the tissue of an internal organ of a patient may be made available for a medical examination or therapy procedure through a natural orifice or an incision to expose the internal organ. Such a procedure may be performed by delivering probe light to the tissue via an endoscope instrument or catheter to reduce or minimize the degree of invasiveness of a diagnostic or therapeutic procedure. At the distal end of the instrument, light is pointed to certain direction or steered to interact with an area or a slice of tissue of interest.

Various devices and techniques based on optical coherence domain reflectometry (OCDR) may be used for non-invasive optical probing of various substances, including but not limited to skins, body tissues and organs of humans and animals, to provide tomographic measurements of these substances. In many OCDR systems, the light from a light source is split into a sampling beam and a reference beam which propagate in two separate optical paths, respectively. The light source may be partially coherent source. The sampling beam is directed along its own optical path to impinge on the substances under study, or sample, while the reference beam is directed in a separate path towards a reference surface. The beams reflected from the sample and from the reference surface are then brought to overlap with each other to optically interfere. Because of the wavelength-dependent phase delay, the optical interference results in no observable interference fringes unless the two optical path lengths of the sampling and reference beams are similar. This provides a physical mechanism for ranging. A beam splitter may be used to split the light from the light source and to combine the reflected sampling beam and the reflected reference beam for detection at an optical detector. The application of OCDR in medical diagnoses in certain optical configurations has come to be known as "optical coherence tomography" (OCT).

SUMMARY

This application includes implementations and examples of techniques, apparatus and systems that use an optical probe head in an endoscope device to optically measure a target for various applications, including techniques, apparatus and systems that use an optical probe head to deliver light to a target and to collect light from the target for imaging and monitoring a target while a separate radiation is applied to treat the target.

In one aspect, an implementation of an endoscope device includes an optical catheter comprising an optical fiber to guide an optical imaging beam and an optical probe head, located at a distal end of the fiber to direct the optical imaging beam from the fiber to a target and to receive light returned from the target under illumination of the optical imaging beam; a detection module to process the light returned from the target under illumination of the optical imaging beam to measure a temperature at a location illuminated by the optical imaging beam; an energy source that produces energy that is applied to the target to raise a temperature at a location of the target where the energy is applied; and a control mechanism that controls the energy source to set a power level of the energy produced by the energy source based on the measured temperature from the detection module.

In another aspect, an implementation of a method for guiding the application of a thermotherapeutic radiation to a target tissue uses an optical catheter comprising an optical fiber to guide an optical imaging beam to direct the optical imaging beam from the fiber to a target and to receive light returned from the target under illumination of the optical imaging beam, processes the light returned from the target tissue under illumination of the optical imaging beam to measure a temperature at a location illuminated by the optical imaging beam; applies a thermotherapeutic energy to the target tissue to raise a temperature at a location of the target tissue where the energy is applied; and controls an amount of the thermotherapeutic energy applied to the target tissue, based on the measured temperature by using the optical imaging beam, to control the temperature at the target tissue between a low limit above which a thermotherapeutic effect is present and a high limit above which a damage to the target tissue occurs.

In yet another aspect, an implementation of an endoscope device for providing guided thermotherapy includes an endoscope tube comprising a hollow working channel and an optical catheter comprising an optical fiber located inside the hollow working channel to guide an optical probe beam and, an optical probe head, located at a distal end of the fiber, to reflect a first portion of the optical probe beam back to the fiber and to direct a section portion of the optical probe beam to a target tissue as an optical imaging beam. The optical probe head receives light returned from the target tissue under illumination of the optical imaging beam to overlap the light returned from the target tissue with the first portion to co-propagate in the fiber away from the optical probe head. This device includes an optical delay device coupled to the fiber to receive the first portion and the light returned from the target tissue to produce a variable relative phase delay between the first portion and the light returned from the target tissue; an optical detector that detects the light of the first portion and the light returned from the target tissue from the optical delay device; a processing unit to receive output from the optical detector and to extract a temperature at a location illuminated by the optical imaging beam from information of the target carried by the light returned from the target tissue; an RF applicator engaged to the endoscope tubing and near the optical probe head to apply RF energy to the target tissue to raise a temperature at a location of the target where the RF energy is applied; and a control mechanism that controls an amount of the RF energy to be applied by the RF applicator to the target tissue based on the measured temperature.

These and other aspects of various techniques, apparatus and systems are described in detail in the drawings, the description and the claims.

BRIEF DESCRIPTION OF THE DRAWINGS

FIGS. 1A and 1B show an example of an endoscope for applying an optical imaging beam and RF radiation to a target in various applications, including using as a bronchoscope bronchial thermoplasty.

DETAILED DESCRIPTION

Figure 2:
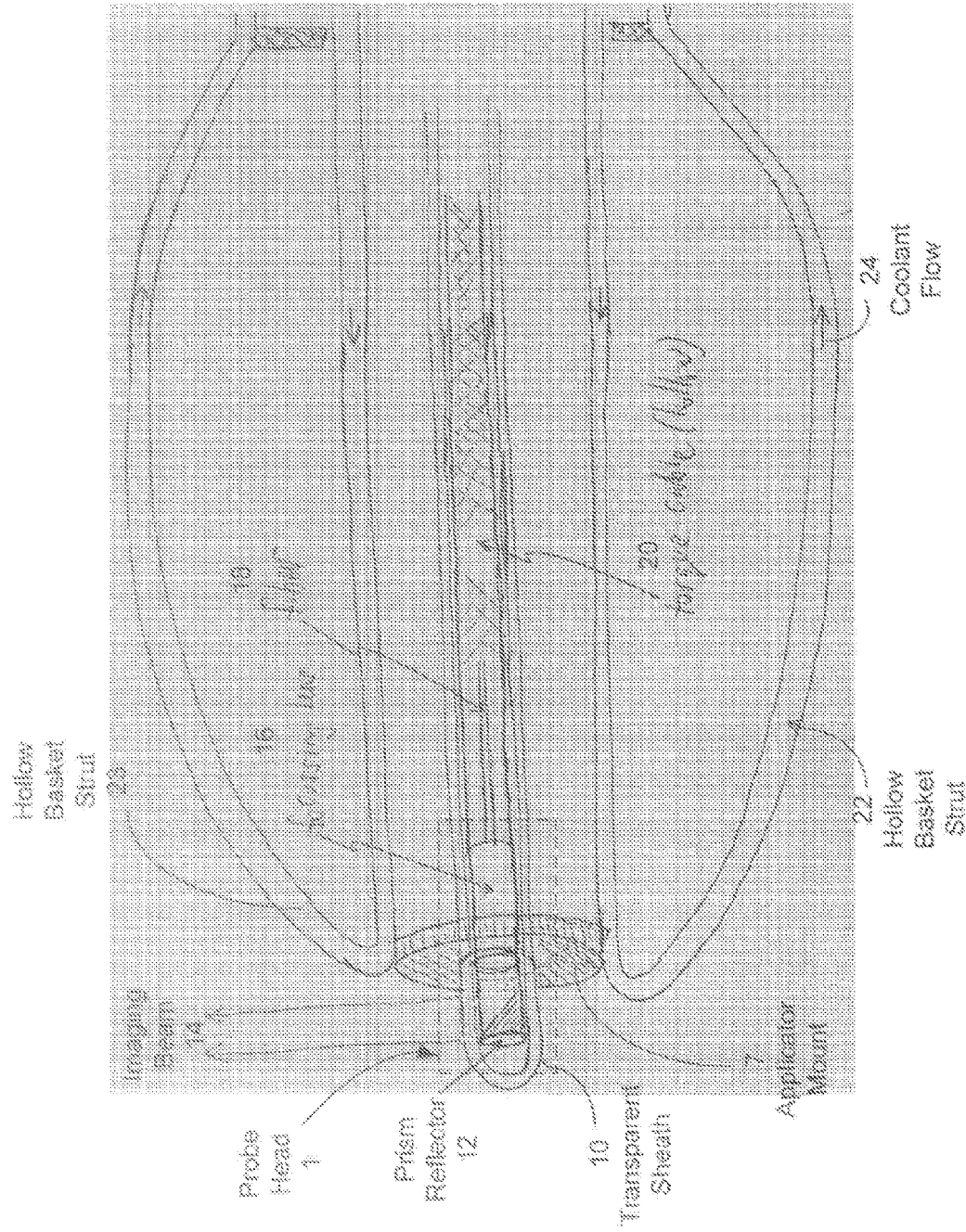
FIG. 2 shows an example of an endoscope for applying an optical imaging beam and RF radiation to a target with a cooling mechanism.

This application describes examples of techniques, apparatus and systems that use optical imaging to achieve temperature profile mapping in various applications, including a thermotherapy process. One example of thermotherapy processes is radio frequency (RF) Ablation (RFA) that uses RF energy to destroy malignant cells via thermal treatment and heating. Thermotherapy depends on achieving a proper temperature range to achieve desired cell necrosis efficacy. If a malignancy is being treated using RFA such as treating liver cancer, RF power levels sufficient to produce complete cell necrosis must be employed. If the power level is too low, incomplete necrosis will occur increasing the likelihood of recurrence. If power levels are too high, extensive charring of the tissues result, impairing recovery. Mapping of the tissue temperature profile during thermotherapy is therefore very important to achieve optimum clinical outcomes.

Endoscope devices described here use light-based tomographic imaging and temperature-induced optical property changes to provide temperature profile mapping of a target, such as tissue, an organ or other object.

For temperatures above normal body temperature, the mass density of water (in grams/cc) decreases as temperature increases. Although the density change is not large, sufficiently sensitive instruments and sufficiently sophisticated interpretative techniques can detect and interpret mass density changes in the water content of soft tissues. When heat is then applied to the tumor to elevate the local tissue temperature to approach 42° C., the process of cell death begins. As the tissue temperature increases the time required to assure cell death decreases. At about 58° C. proteins begin to denature and at higher temperatures tissue coagulates. The denaturation and coagulation of tissue contained within approximately the same volume, produces density changes. As heat is transported from the central coagulation zone and conducted to surrounding tissues, an expanding coagulation zone develops and increases as a function of thermal power delivered over time. The primary treatment for both malignant and benign tumors is surgery. While surgery has proven to be effective in cancer treatment, it is expensive and invasive, frequently requiring lengthy hospital stays for patient recovery. A critical measure of surgical success is the complete removal of the tumor with surgical margins testing negative to tumor cells upon pathology review.

With the number of cancer cases steadily increasing throughout the world, a less invasive, less costly way of treating primary and metastatic tumors is desired. Modern diagnostic imaging modalities and new interventional methods have set the stage for bringing less invasive methods to the field of oncology treatment much as imaging has enabled the diagnosis and minimally invasive treatment of coronary arteries with balloon catheters and drug eluting stents.

The devices and techniques described in this document combines real time imaging with interventional access to solid tumors offers the possibility to non surgically treat, or ablate, the tumor mass. Improved minimally invasive methods are being developed to treat both primary and metastatic solid tumors. The present devices and techniques can be used to create thermal injury to tissue when used in conjunction with a percutaneous approach to the lesion. The energy sources used of creating the desired thermal injury can vary depending on implementations and may use RF (radiofrequency), laser, microwave energy or high intensity focused ultrasound.

While thermal ablative techniques such as radiofrequency ablation or laser ablation are rapidly gaining acceptance in the treatment of inoperable tumors, incomplete treatments are common since there is no reliable method to monitor the treatment zone during the ablation. A treatment that does not encompass the entire tumor will result in recurrent growth of the tumor, usually within one or two years. Ablative techniques will be held back from full adoption as long as the treatment zone cannot be monitored during the ablation.

The present optical imaging devices and techniques provide optical monitoring and feedback control for thermal therapy. Various aspects of the such devices and techniques can be found in PCT Application No. PCT/US2005/37730 (PCT Publication No. WO 2006/045013) entitled "Integrated Disease Diagnosis and Treatment System" which is incorporated by reference as part of the disclosure of this document. Such optical imaging systems can be used for mapping of spatially non-uniform thermal distributions and can have special utility in thermotherapies where microstructural imaging plays an important role. As an example, bronchial wall microstructure is very important in a new, non-drug asthma thermotherapy called Bronchial Thermoplasty while, in various CT-guided RFA therapy, low resolution CT imaging is performed at a low rate of CT imaging and thus is inadequate for real time monitoring of RFA therapy. The present optical imaging devices provide fast imaging of the target tissue under treatment, e.g., 30 images/sec, and thus can be used to measure the thermal effect caused by the RF radiation during the RF treatment.

Bronchial Thermoplasty [BT] is a non-drug asthma therapy in clinical trials and has been developed over the past seven years as a means of reducing the severity of asthmatic exacerbations in patients whose asthma is not well controlled by cortico-steroid or anti-inflammatory inhalers. BT uses RF energy, applied to the airway smooth muscle [ASM], which surrounds the bronchus in a somewhat random pattern, to reduce the ability of the ASM to contract and obstruct airflow. The RF catheter is inserted into the working channel of a bronchoscope and positioned in a secondary/tertiary bronchus, but since the ASM is not visible from within the bronchus, there is no way to position the RF electrode in close proximity to the ASM. As a consequence, RF energy is applied periodically, as the catheter is withdrawn from the bronchus, and, on the average, damages some of the ASM to some degree. An interesting statistic is that ASM covers, on the average, only 2.5-4.5% of the surface of a major airway. The procedure does provide relief, but in all likelihood, could be more effective if microstructural cross-sectional imaging allowed the physician to accurately position the RF electrode directly above the ASM. In addition, some patients experience adverse events [including hospitalization] after BT. Since the same treatment parameters are used for each patient, it seems reasonable to conclude that differences in bronchial wall microanatomy may be responsible for these adverse events.

The optical imaging systems described in this document can be used to play the role of a companion diagnostic for BT as well as providing procedural imaging for guidance and control.

FIGS. 1A and 1B below show an example endoscope apparatus that combines the optical imaging for thermal mapping and RFA mechanism. This endoscope device includes an optical catheter 4 comprising an optical fiber 18 to guide an optical imaging beam 14 and an optical probe head 1, located at a distal end of the fiber 18 to direct the optical imaging beam 14 from the fiber 18 to a target and to receive light returned from the target under illumination of the optical imaging beam 14. The optical probe head 1 as illustrated in this example includes a prism reflector 12 and the distal end facet of the fiber 18 and may be implemented in other configurations. The optical probe head 1 is fixed to the distal end of the fiber 18. The fiber 18 is attached to a torque cable that can rotate the fiber 18 and thus the optical probe head 1 to allow the optical imaging beam 14 from the optical probe head 1 to scan around at different positions. In addition, the torque cable can be used to push or pull the optical probe head 1 to different positions long the longitudinal direction of the fiber 18. Therefore, under this design, the optical probe head 1 can be used to sense images at different locations along the longitudinal direction of the fiber 18 and, at each location, the optical probe head 1 can be rotated to sense the surrounding areas at different directions.

In this device, a detection module is provided to process the light returned from the target under illumination of the optical imaging beam 14 to measure a temperature at a location illuminated by the optical imaging beam 14. An energy source is provided to produce energy that is applied to the target to raise a temperature at a location of the target where the energy is applied. In this example, the energy source is an RF source and an RF applicator 6 is provided to direct the RF energy to the target. A control mechanism is also provided to control the energy source to set a power level of the energy produced by the energy source based on the measured temperature from the detection module.

An endoscope tube or sheath 2 with a hollow working channel is provided to house the fiber 18 and to hold the RF applicator 6 and an RF transmission path 8 that connects the RF applicator 6 and the RF source. The RF transmission path 8 can be an electrically conductive tube in some implementations. When implemented as a bronchoscope, the endoscope tube 2 may include other components such as an imaging camera and a biopsy module. The RF applicator 6 can be an RF conductive wires in form of a basket and is attached to an outer sheath 10 outside the optical fiber 18 in the optical catheter 14 in a way that allows the basket to expand when the outer sheath 10 is pulled in the endoscope tube or sheath 2. It is a sliding fit so that the optical imaging catheter 4 can rotate within the endoscope sheath 2 to form the image. As illustrated, an applicator mount 7 is provided to engage the RF applicator 6 to the outer sheath 10. The optical catheter 4 also may be moved in a longitudinal manner, to image proximally, distally or exactly at the point where the basket struts contact the airway wall tissue. The configuration is such that the coaxial imaging catheter 4 can rotate inside the sheath 10 which is fixed to the basket applicator 6 at the tip. The sheath/imaging catheter unit is initially extended to allow the collapsed wire RF applicator basket 6 to fit through the working channel orifice as used in bronchoscopes and other endoscopes. The size may not be so critical in this particular example as the RF Bronchial Thermoplasty therapy is used in the larger airways.

FIG. 2 shows another example of an endoscope where the optical probe head 1 of the optical catheter 4 includes a prism reflector 12 and a focusing lens 16 that provide optical focusing between the prism reflector 12 and the distal end of the fiber 18. The focusing lens 16 or its interface with the distal end of the fiber 18 can be used by the optical probe head 1 to reflect a first portion of an optical probe beam guided by the fiber 18 towards the optical probe head back to the fiber 18 and to direct a section portion of the optical probe beam to a target tissue as the optical imaging beam 14. The prism reflector 12, the focusing lens 16 and the distal end of the fiber 18 are fixed in position relative to each other and rotate or move together as the fiber 18 is rotated or moved by a torque cable 20 attached to the fiber 18. The optical probe head 1 receives light returned from the target tissue under illumination of the optical imaging beam 14 to overlap the light returned from the target tissue with the first portion that does not reach the target tissue to co-propagate in the fiber 18 away from the optical probe head for optical detection and processing.

In many cases, for example in the case of ASM, the therapeutic area of interest [ASM] occurs below the surface of a target tissue under treatment. In this case, if RF power is applied such that the temperature of the ASM is optimized for cytosis [time/temperature], the airway surface tissue reaches a temperature higher than that of the ASM which may lead to damage and an Adverse Event [AE]. Significant severe AEs are reported after BT therapy [10%]. The endoscope design in FIG. 2 includes a cooling mechanism that cools the surface of the treated target issue to be lower than a temperature underneath the surface. In this regard, a coolant, e.g., a cooling gas or liquid, can be direct to pass near the tissue surface to cool the surface. As a specific example, the conductive struts of the RF basket applicator can be made from flexible hollow tubing which carries the cooling gas or liquid. When a liquid coolant is used, a loop for carrying the liquid coolant is need to direct the coolant out of the endoscope. When a gaseous coolant is used, the gaseous coolant may be directed to the target surface without being collected. In FIG. 2, two hollow basket struts 22 and 23 are used to form two cooling loops near the tip of the endoscope which a coolant is passed. An applicator mount 7 is provided to hold the hollow basket struts 22 and 23 relative to the sheath 10. This design can reduce the surface temperature of the contact region of the target tissue and the peak temperature of the treated location on the target issue occurs at some distance below the surface, depending on the coolant used, and its temperature and flow rate. This places the peak temperature in closer proximity to the target ASM, resulting in improved therapeutic efficacy.

When the above described endoscope is used as a bronchoscope for BT treatment, an image can be acquired from each bronchial location, e.g., over a 1-second imaging time. During BT local tissue temperatures rise and when approaching approximately 40° C. the process of cell death begins. As the tissue temperature increases the time required to assure cell death decreases. Between about 55-60° C. proteins begin to lose water and at even higher temperatures tissue chars, producing density changes. During the RF power application interval, heat is conducted to surrounding tissues, expanding the tissue damage zone as a function of RF energy [RF power×time]. Periodic tomographic images may be taken at frequent intervals (e.g., few seconds) to monitor process temperature and/or ASM condition.

After suitable pilot studies have been performed to establish to the correlation between adverse events and unique microstructural features [e.g. location/extent of ASM, submucosal position/thickness] it will be possible to make therapeutic decisions and set therapeutic parameters based on pre-therapeutic imaging results. This should allow physicians to utilize optimum RF power settings to achieve efficacy while minimizing the number and extent of adverse events. Since BT changes the water content and hence the optical properties of ASM, BT induced ASM damage can be ascertained by comparing pre- and post-therapy microstructure images. A growing experience base will allow physicians to personalize therapeutic parameters to obtain the best clinical outcome for the patient. This ability includes locating the ASM as well as temperature/tissue monitoring during RF power application at each site.

Figure 3:
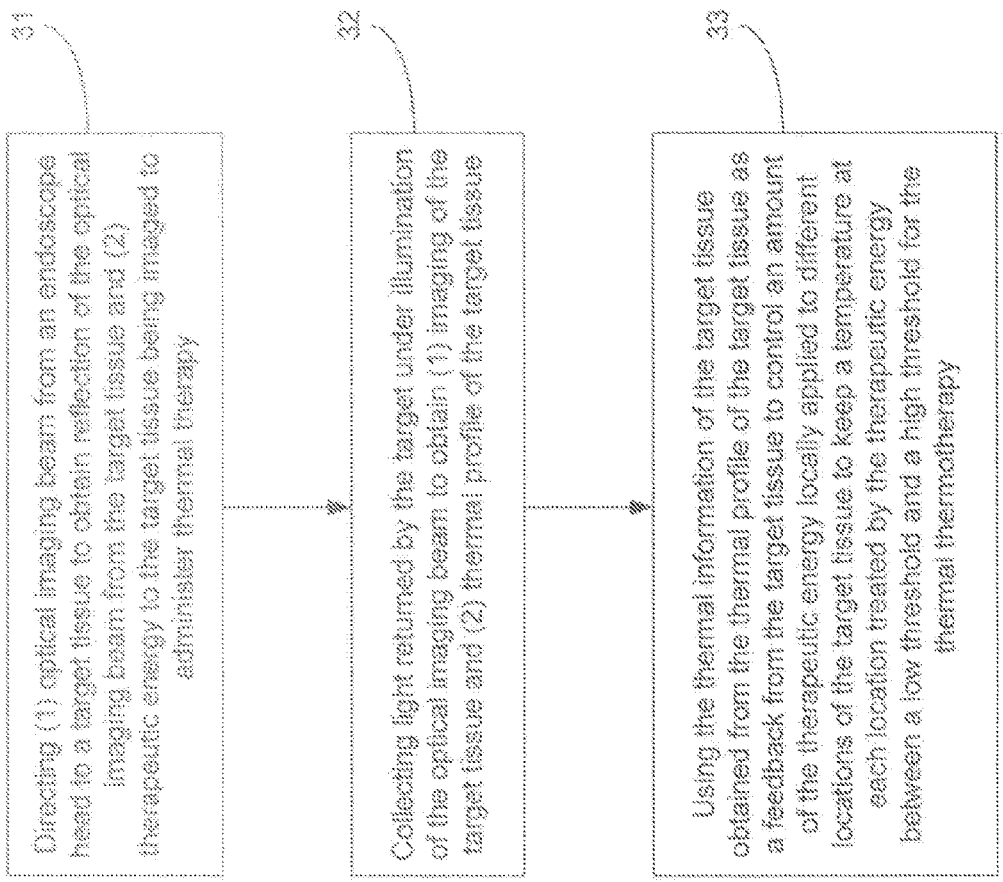
FIG. 3 shows one operation of the endoscope in FIGS. 1A and 1B or in FIG. 2.

The optical catheter 4 in the endoscope in FIGS. 1A and 1B or FIG. 2 can be used to obtain both (1) imaging of the target tissue and (2) thermal profile of the target tissue. The imaging information allows the physician to inspect the images of a treat area and the thermal profile of the target issue allows proper control of the delivery of the RF power for thermotherapy to achieve effect treatment without damaging the tissue. FIG. 3 shows one exemplary process for operating the endoscope in FIGS. 1A and 1B or FIG. 2. First, an optical imaging beam is directed from the endoscope head to the target tissue to obtain reflection of the optical imaging beam from the target tissue and the therapeutic energy is directed to the target tissue being imaged to administer thermal therapy (step 31). Next, the light returned by the target under illumination of the optical imaging beam is collected and processed to obtain (1) imaging of the target tissue and (2) thermal profile of the target tissue (step 32). The thermal information of the target tissue obtained from the thermal profile of the target tissue is used as a feedback from the target tissue to control an amount of the therapeutic energy locally applied to different locations of the target tissue to keep a temperature at each location treated by the therapeutic energy between a low threshold and a high threshold for the thermal thermotherapy (step 33).

In some implementations, the optical probe head 1 can be used to do an imaging scan of the entire treatment area, e.g., performing imaging the surrounding area at each location of the optical probe head 1 along the longitudinal direction of the fiber 18 and repeating this imaging operation at different locations in the longitudinal direction of the fiber 18. This pre-treatment imaging scan allows construction of an imaging map of the entire area to be treated and identification of selected locations in the entire area to be treated. This pre-treatment imaging scan can be used as a map to control and guide the application of the thermotherapy radiation to the selected locations. During treatment at each of the selected locations, the optical probe head 1 is used to monitoring the thermal profile at each selected location and the monitoring result is used to control the power lever of the thermotherapy radiation being applied. Alternatively, in other implementations, the optical probe head 1 can be directed to each location of the entire treatment area to perform an imaging scan by rotating the optical probe head 1 to detect whether there is a target area to be treated and then perform the radiation treatment if a target area is detected. Then the optical probe head 1 is moved along the longitudinal direction of the fiber 18 to a different location to repeat the optical imaging for detecting one or more targets and then radiation treatment of each detected target. During the radiation treatment, the optical probe head 1 is used to monitoring the thermal profile at each selected location and the monitoring result is used to control the power lever of the thermotherapy radiation being applied.

FIGS. 4-8 show examples of an optical catheter 4 for directing the optical imaging beam 14 to the target in the endoscope in FIGS. 1A and 1B or in FIG. 2 and associated optical detection and processing. The optical probe head reflects a first portion of an optical probe beam back to the fiber and to direct a section portion of the optical probe beam to a target tissue as the optical imaging beam and further receives light returned from the target tissue under illumination of the optical imaging beam to overlap the light returned from the target tissue with the first portion to co-propagate in the fiber away from the optical probe head. Such design allows for superposition and interplay of different optical waves and modes propagating along substantially the same optical path provided by the fiber 18. When one of the optical waves or modes interacts with the target, its superposition with another wave or mode can be used for acquiring information about the optical properties of the substance. This use of a common optical path for different optical waves which may be in the same mode or different modes avoids separation of the reference light beam from the sample light beam in various optical coherence domain reflectometry (OCDR) systems and associated technical issues caused by the separation of optical paths such as uncontrolled fluctuations in the relative optical phase or differential delay between the two beams that may adversely affect the measurements. The use of the common optical path for different optical waves in the same or different modes may be advantageously used to stabilize the relative phase among different radiation waves and modes in the presence of environmental fluctuations in the system such as variations in temperatures, physical movements of the system especially of the waveguides, and vibrations and acoustic impacts to the waveguides and system. In this context, such systems have a "built-in" stability of the differential optical path by virtue of their optical designs and are beneficial for some phase-sensitive measurement, such as the determination of the absolute reflection phase and birefringence.

Figure 4:
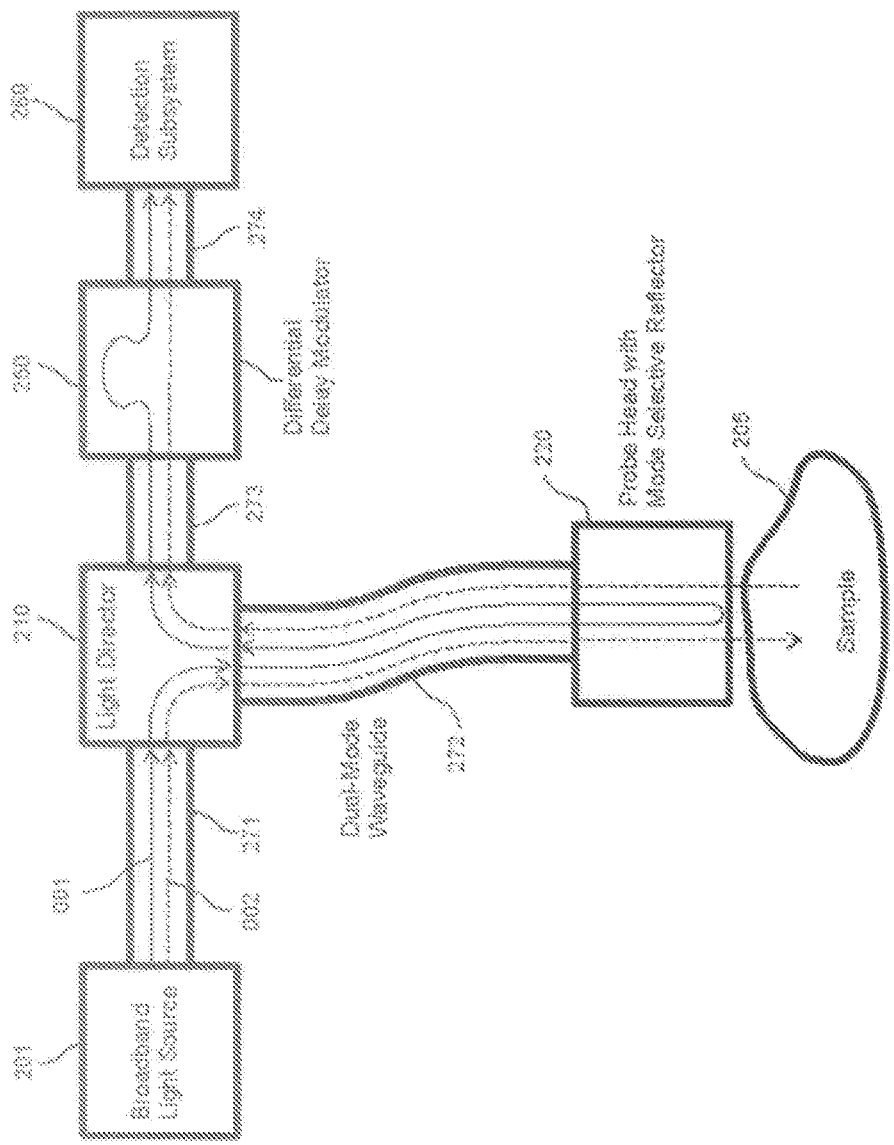
FIGS. 4-8 show examples of an optical catheter for directing the optical imaging beam to the target in the endoscope in FIGS. 1A and 1B or in FIG. 2 and associated optical detection and processing, where the optical probe head reflects a first portion of an optical probe beam back to the fiber and to direct a section portion of the optical probe beam to a target tissue as the optical imaging beam and further receives light returned from the target tissue under illumination of the optical imaging beam to overlap the light returned from the target tissue with the first portion to co-propagate in the fiber away from the optical probe head.

FIG. 4 shows one example of a sensing device according to one implementation. This device directs light in two propagation modes along the same waveguide to an optical probe head near a sample 205 for acquiring information of optical inhomogeneity in the sample. A sample holder may be used to support the sample 205 in some applications. Light radiation from a broadband light source 201 is coupled into the first dual-mode waveguide 271 to excite two orthogonal propagation modes, 001 and 002. A light director 210 is used to direct the two modes to the second dual-mode waveguide 272 that is terminated by a probe head 220. The probe head 220 may be configured to perform at least the following functions. The first function of the probe head 220 is to reverse the propagation direction of a portion of light in the waveguide 272 in the mode 001; the second function of the probe head 220 is to reshape and deliver the remaining portion of the light in mode 002 to the sample 205; and the third function of the probe head 220 is to collect the light reflected from the sample 205 back to the second dual-mode waveguide 272. The back traveling light in both modes 001 and 002 is then directed by light director 210 to the third waveguide 273 and further propagates towards a differential delay modulator 250. The differential delay modulator 250 is capable of varying the relative optical path length and optical phase between the two modes 001 and 002. A detection subsystem 260 is used to superpose the two propagation modes 001 and 002 to form two new modes, mutually orthogonal, to be received by photo-detectors. Each new mode is a mixture of the modes 001 and 002.

The superposition of the two modes 001 and 002 in the detection subsystem 260 allows for a range detection. The light entering the detection subsystem 260 in the mode 002 is reflected by the sample, bearing information about the optical inhomogeneity of the sample 205, while the other mode, 001, bypassing the sample 205 inside probe head 220. So long as these two modes 001 and 002 remain independent through the waveguides their superposition in the detection subsystem 260 may be used to obtain information about the sample 205 without the separate optical paths used in some conventional Michelson interferometer systems.

For the simplicity of the analysis, consider a thin slice of the source spectrum by assuming that the amplitude of the mode 001 is $E_{001}$ in a first linear polarization and that of the mode 002 is $E_{002}$ in a second, orthogonal linear polarization in the first waveguide 271. The sample 205 can be characterized by an effective reflection coefficient r that is complex in nature; the differential delay modulator 250 can be characterized by a pure phase shift $\Gamma$ exerted on the mode 001. Let us now superpose the two modes 001 and 002 by projecting them onto a pair of new modes, $E_A$ and $E_B$, by a relative 45-degree rotation in the vector space. The new modes, $E_A$ and $E_B$, may be expressed as following:

$$\begin{cases} E_A = \frac{1}{\sqrt{2}}(e^{j\Gamma}E_{001} + rE_{002}); \\ E_B = \frac{1}{\sqrt{2}}(e^{j\Gamma}E_{001} - rE_{002}). \end{cases} \quad (1)$$

It is assumed that all components in the system, except for the sample 205, are lossless. The resultant intensities of the two superposed modes are $$\begin{cases} I_A = \frac{1}{2}[E_{001}^2 + E_{002}^2 + |r|E_{001}E_{002}\cos(\Gamma - \varphi)]; \\ I_B = \frac{1}{2}[E_{001}^2 + E_{002}^2 - |r|E_{001}E_{002}\cos(\Gamma - \varphi)], \end{cases} \quad (2)$$

where $\varphi$ is the phase delay associated with the reflection from the sample. A convenient way to characterize the reflection coefficient r is to measure the difference of the above two intensities, i.e.

$$I_A - I_B = |r|E_{001}E_{002}\cos(\Gamma - \varphi) \quad (3)$$

If $\Gamma$ is modulated by the differential delay modulator 250, the measured signal, Eq. (3), is modulated accordingly. For either a periodic or a time-linear variation of $\Gamma$, the measured signal responds with a periodic oscillation and its peak-to-peak value is proportional to the absolute value of r.

For a broadband light source 201 in FIG. 2, consider the two phases, $\Gamma$ and $\varphi$ to be dependent on wavelength. If the two modes 001 and 002 experience significantly different path lengths when they reach the detection system 260, the overall phase angle, $\Gamma-\varphi$, should be significantly wavelength dependant as well. Consequently the measured signal, being an integration of Eq. (3) over the source spectrum, yields a smooth function even though $\Gamma$ is being varied. The condition for a significant oscillation to occur in the measured signal is when the two modes 001 and 002 experience similar path lengths at the location of their superposition. In this case the overall phase angle, $\Gamma-\varphi$, becomes wavelength independent or nearly wavelength independent. In other words, for a given relative path length set by the modulator 250, an oscillation in the measured signal indicates a reflection, in the other mode, from a distance that equalizes the optical path lengths traveled by the two modes 001 and 002. Therefore the system depicted in FIG. 2 can be utilized for ranging reflection sources.

Due to the stability of the relative phase between the two modes, 001 and 002, phase-sensitive measurements can be performed with the system in FIG. 2 with relative ease. The following describes an exemplary method based on the system in FIG. 2 for the determination of the absolute phase associated with the radiation reflected from the sample 205.

In this method, a sinusoidal modulation is applied to the differential phase by the differential delay modulator 250, with a modulation magnitude of M and a modulation frequency of $\Omega$. The difference in intensity of the two new modes is the measured and can be expressed as follows:

$$I_A - I_B = |r|E_{001}E_{002}\cos[M\sin(\Omega t)-\varphi]. \quad (4)$$

It is clear from Eq. (4) that the measured exhibits an oscillation at a base frequency of $\Omega$ and oscillations at harmonic frequencies of the base frequency $\Omega$. The amplitudes of the base frequency and each of the harmonics are related to $\varphi$ and $|r|$. The relationships between r and the harmonics can be derived. For instance, the amplitude of the base-frequency oscillation and the second harmonic can be found from Eq. (4) to be:

$$A_\Omega = E_{001}E_{002}J_1(M)|r|\sin\varphi; \quad (5a)$$

$$A_{2\Omega} = E_{001}E_{002}J_2(M)|r|\cos\varphi, \quad (5b)$$

where $J_1$ and $J_2$ are Bessel functions of the first and second order, respectively. Eq. (5a) and (5b) can be used to solve for $|r|$ and $\varphi$, i.e. the complete characterization of r. We can therefore completely characterize the complex reflection coefficient r by analyzing the harmonic content of various orders in the measured signal. In particular, the presence of the base-frequency component in the measured is due to the presence of $\varphi$.

Figure 5:
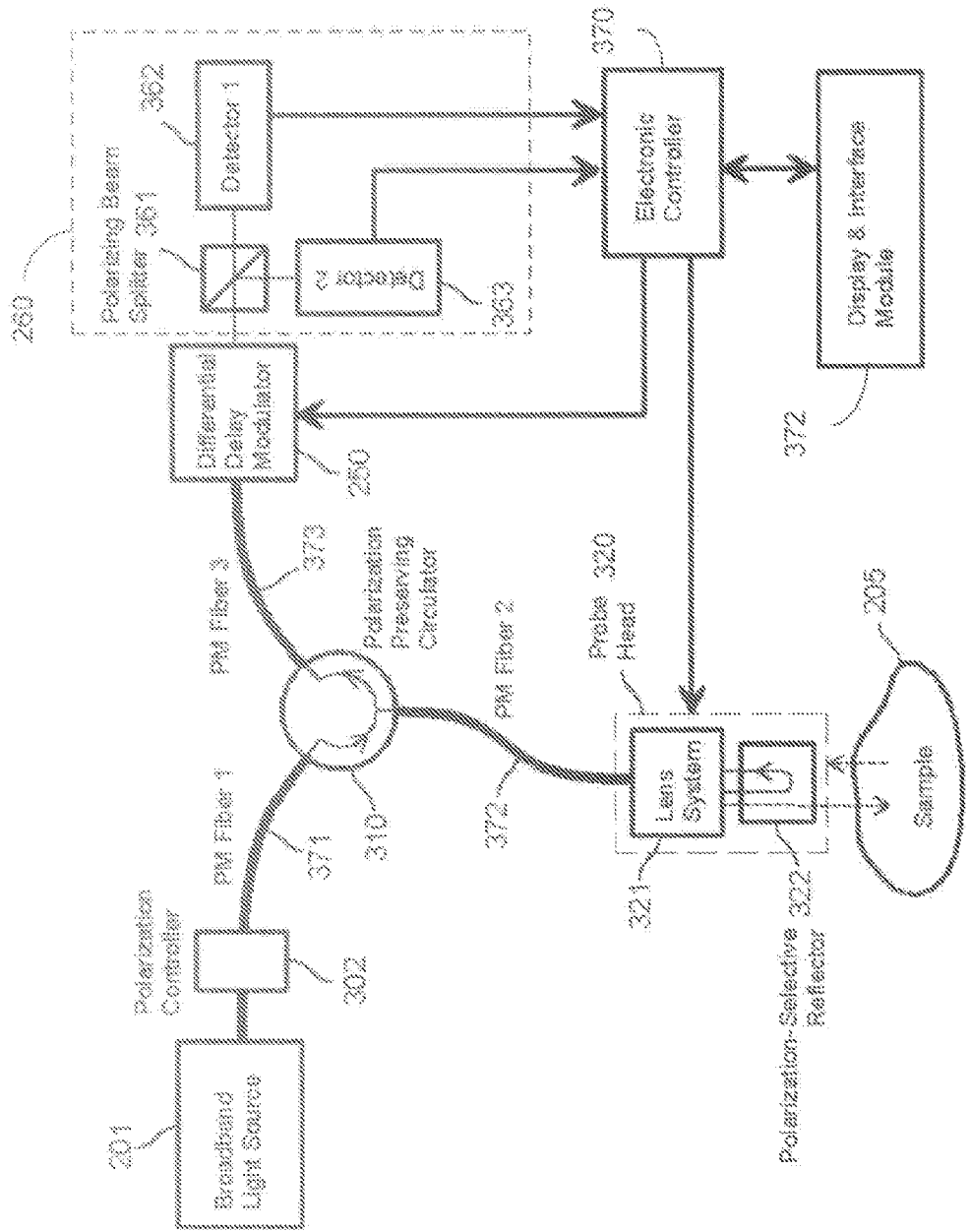

FIG. 5 shows an exemplary implementation of the system depicted in FIG. 4. The spectrum of source 201 may be chosen to satisfy the desired ranging resolution. The broader the spectrum is the better the ranging resolution. Various light sources may be used as the source 201. For example, some semiconductor superluminescent light emitting diodes (SLED) and amplified spontaneous emission (ASE) sources may possess the appropriate spectral properties for the purpose. In this particular example, a polarization controller 302 may be used to control the state of polarization in order to proportion the magnitudes of the two modes, 001 and 002, in the input waveguide 371. The waveguide 371 and other waveguides 372 and 373 may be dual-mode waveguides and are capable of supporting two independent polarization modes which are mutually orthogonal. One kind of practical and commercially available waveguide is the polarization maintaining (PM) optical fiber. A polarization maintaining fiber can carry two independent polarization modes, namely, the s-wave polarized along its slow axis and the p-wave polarized along its fast axis. In good quality polarization maintaining fibers these two modes can have virtually no energy exchange, or coupling, for substantial distances. Polarization preserving circulator 310 directs the flow of optical waves according to the following scheme: the two incoming polarization modes from fiber 371 are directed into the fiber 372; the two incoming polarization modes from fiber 372 are directed to the fiber 373. A polarization-preserving circulator 310 may be used to maintain the separation of the two independent polarization modes. For instance, the s-wave in the fiber 371 should be directed to the fiber 372 as s-wave or p-wave only. Certain commercially available polarization-preserving circulators are adequate for the purpose.

The system in FIG. 5 implements an optical probe head 320 coupled to the waveguide 372 for optically probing the sample 205. The probe head 320 delivers a portion of light received from the waveguide 372, the light in one mode (e.g., 002) of the two modes 001 and 002, to the sample 205 and collects reflected and back-scattered light in the same mode 002 from the sample 205. The returned light in the mode 002 collected from the sample 205 carries information of the sample 205 and is processed to extract the information of the sample 205. The light in the other mode 001 in the waveguide 372 propagating towards the probe head 320 is reflected back by the probe head 320. Both the returned light in the mode 002 and the reflected light in the mode 001 are directed back by the probe head 320 into the waveguide 372 and to the differential delay modulator 250 and the detection system 260 through the circulator 310 and the waveguide 373.

In the illustrated implementation, the probe head 320 includes a lens system 321 and a polarization-selective reflector (PSR) 322. The lens system 321 is to concentrate the light energy into a small area, facilitating spatially resolved studies of the sample in a lateral direction. The polarization-selective reflector 322 reflects the mode 001 back and transmits the mode 002. Hence, the light in the mode 002 transmits through the probe head 320 to impinge on the sample 205. Back reflected or scattered the light from the sample 205 is collected by the lens system 321 to propagate towards the circulator 310 along with the light in the mode 001 reflected by PSR 322 in the waveguide 372.

In the above described examples, the optical probe head sends out light in two different propagation modes where light in one of the two modes carries the information from the sample. Alternatively, light in a single propagation mode may be used as the input light to the optical probe head and as output light from the optical probe head. Hence, devices based on this design not only use a common optical path to direct light to and from the probe head and sample but also control the light in a single mode. In comparison with above examples where two different modes are used for light coming out of the probe heads, this single-mode design further eliminates or reduces any differences between different modes that propagate in the same optical path.

Figure 6:
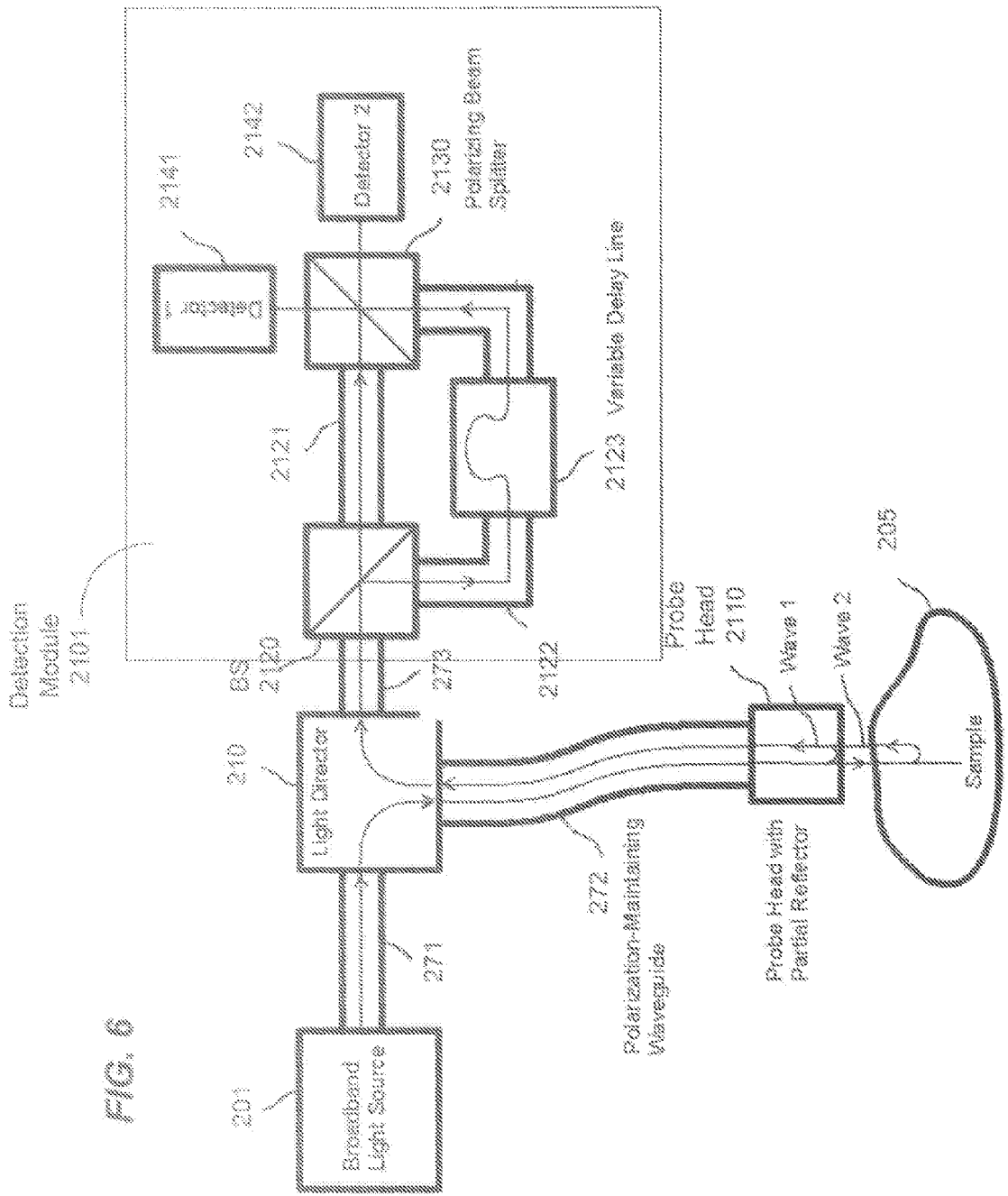

FIG. 6 shows one exemplary system for acquiring information of optical inhomogeneity and other properties in substances with only one propagation mode inside waveguides. A broadband or low-coherence light from Broadband Light Source 201 is directed to a probe head 2110 by means of polarization-maintaining waveguides 271 and 272. A partial reflector inside the probe head 2110 reverses the direction of a small portion of the input light to create a radiation wave 1 while transmitting the remainder of the input light to the sample 205. Backscattered or reflected light from the sample 205 becomes a second radiation wave 2 and is collected by the probe head 2110. The probe head 2110 combines and couples both the radiation waves 1 and 2 back into the waveguide 272. The radiation waves 1 and 2 travel in the waveguide 272 towards Light the light director 210 which directs radiation waves 1 and 2 through the waveguide 273 towards the detection module 2101. Notably, the radiation waves 1 and 2 output from the probe head 2110 are in the same mode as the input light to the probe head 2110. the probe head 2110 does not change the mode of light when directing the radiation waves 1 and 2 to the waveguide 272.

The detection module 2101 includes a beam Splitter 2120, two optical paths 2121 and 2122, an optical variable delay element 2123 in the path 2122, a beam combiner 2130, and two optical detectors 2141 and 2142. The beam splitter 2120 splits the light in the waveguide 273, which includes the radiation waves 1 and 2 in the same mode, into two parts that respectively propagate in the two optical paths 2121 and 2122. Notably, each of the two parts includes light from both the radiation waves 1 and 2. The variable delay element or delay line 2123 in the optical path 2122 is controlled by a control signal to adjust the relative optical delay between the two optical paths 2121 and 2122 and may be implemented by, e.g., the exemplary delay elements described in this application and other delay designs. The beam combiner 2130 combines the signals of the two optical paths to overlap with each other and to output two optical signals for optical detectors 2141 and 2142, respectively. The beam combiner may be a polarization beam splitter which splits the combined light into two parts, orthogonal in polarization to one another.

The probe head 2110 may include a partial reflector to produce the radiation wave 1 which does not reach the sample 205. Assuming the single propagation mode for the light to the probe head 2110 and the light out of the probe head 21110 is a polarization mode, the light reflected from the partial reflector in the probe head 2110, i.e., the radiation wave 1, has the same polarization as the light collected from the sample, the radiation wave 2. Therefore, both Radiation 1 and 2 travel in the same propagation mode in the waveguides, 272 and 273. Because the radiation waves 1 and 2 are reflected from different locations, they experience different optical path lengths when reaching the beam splitter 2120. The effect of variable delay element 2123 is to add an adjustable amount of the delay in the light in the path 2122 relative to the light in the path 2121.

In operation, the variable delay element 2123 can be adjusted so that the partial radiation 1 reaching the polarization beam splitter 2130 through the path 2122 can be made to experience a similar optical path length as the partial radiation 2 reaching the beam splitter 2130 via the other path 2121. The superposition of the two beams at the photo detectors 2141 and 2142 causes a measurable intensity variation as their relative path length is being varied by the variable delay element 2123. This variation can be utilized to retrieve information on the inhomogeneity and other properties of the sample 205.

Figure 7:
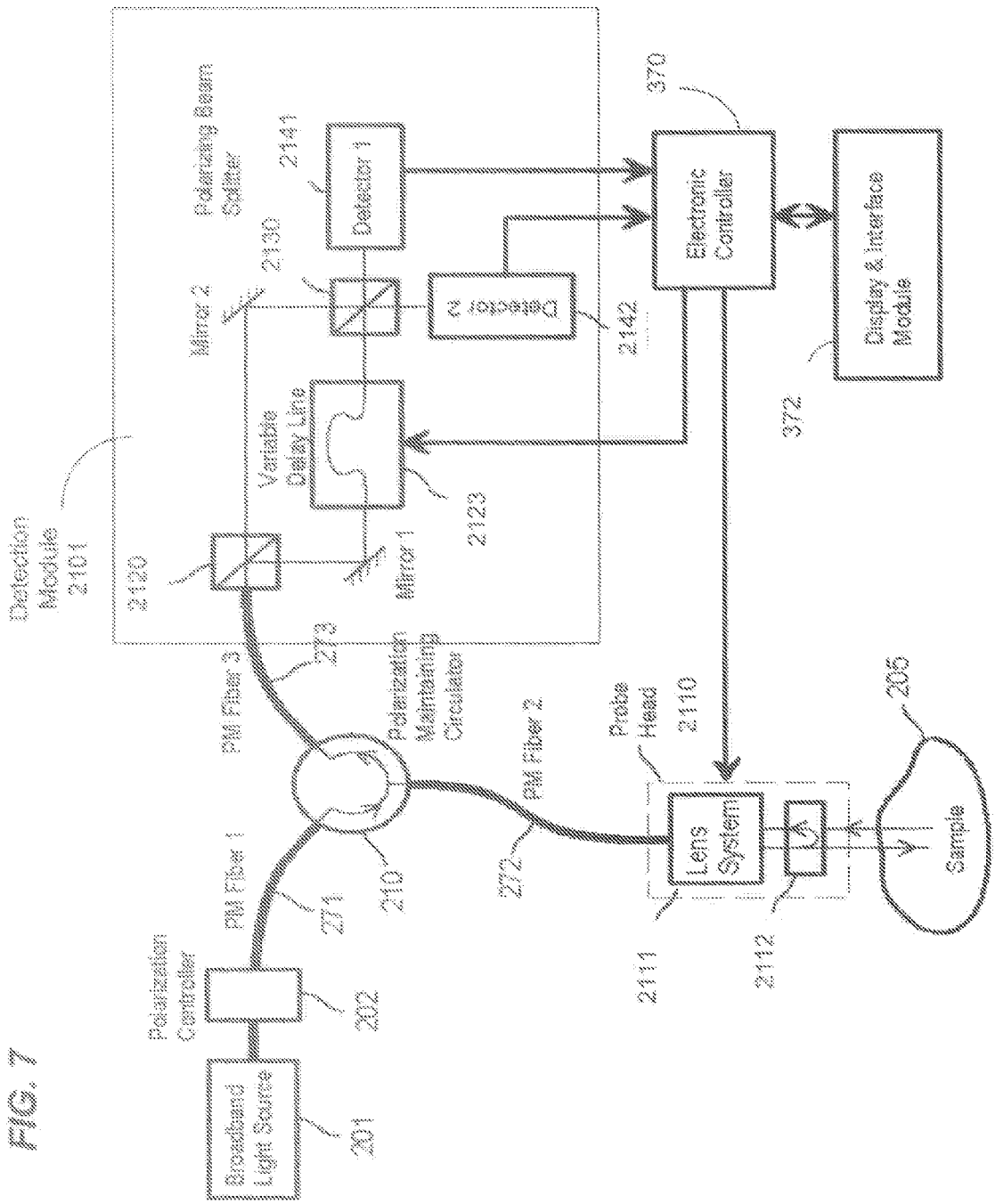

FIG. 7 shows an exemplary implementation of the system in FIG. 6 using polarization maintaining optical fibers. A polarization controller 202 may be placed at the output of the light source 201 to control the polarization of the input light in one polarization mode. The optical head 2110 is shown to include a lens system 2111 and a partial reflector 2112. Two mirrors 1 and 2 are used to construct the two optical paths between the beam splitters 2120 and 2130. The optical radiation reflected from the partial reflector 2122 and from the sample 205 travel in the polarization-maintaining (PM) fiber 272 in the same mode. The main portions of the radiation waves 1 and 2 are deflected to the mirror 1 while the remaining portions are directed to the mirror 2 by the beam splitter 2120.

The incident plane of the polarizing beam splitter 2130 can be made to have a finite angle with respect to the polarization directions of light from both the Mirror 2 in one optical path and the variable delay element 2123 from the other optical path. In this configuration, light energies received by both detectors 2141 and 2142 are the superposition of the two radiations, i.e., Radiation 1 and Radiation 2. It should be appreciated that the linkage between the beam splitters 2120 and 2130 can be made by means of optical fibers or other optical waveguides to eliminate the free space paths and the two mirrors 1 and 2.

In some implementations, the probe head may be designed to cause a first portion of the first mode to reverse its propagation direction while directing the remaining portion, or a second portion, to reach the sample. The reflection or back scattered light of the second portion from the sample is collected by the probe head and is controlled in the second propagation mode different from the first mode to produce a reflected second portion. Both the reflected first portion in the first propagation mode and the reflected second portion in the second propagation mode are directed by the probe head through a common waveguide into the detection module for processing. In comparison with the implementations that use light in two modes throughout the system, this alternative design further improves the stability of the relative phase delay between the two modes at the detection module and provides additional implementation benefits.

Figure 8:
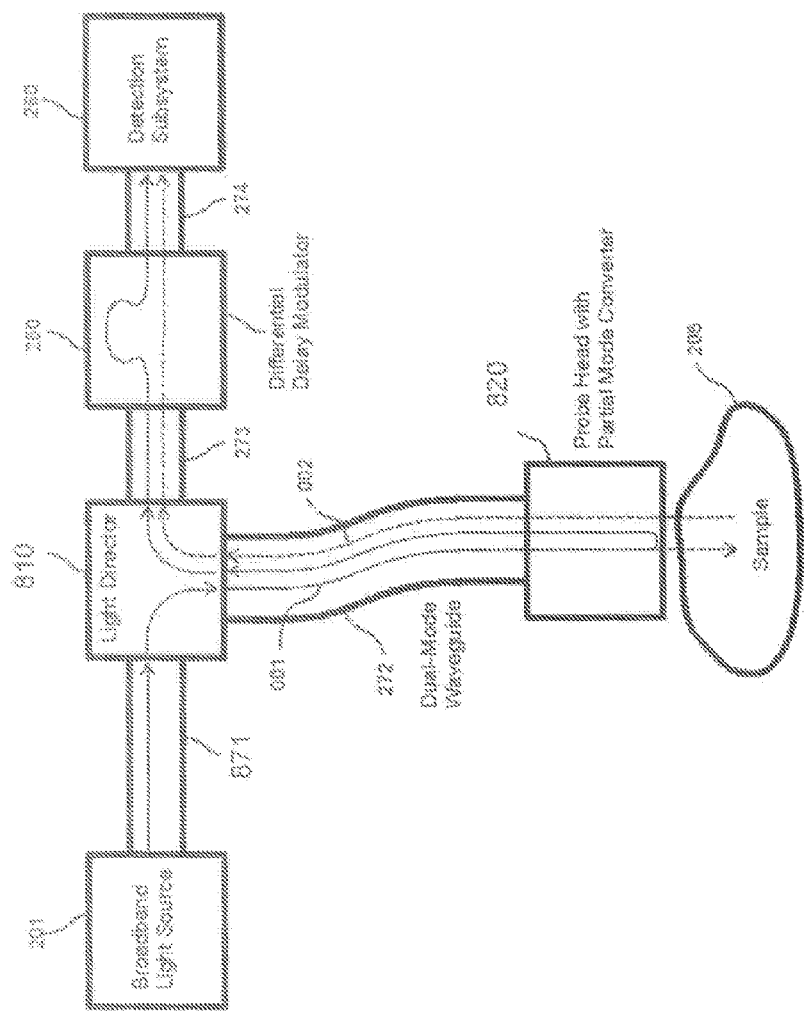

FIG. 8 illustrate one exemplary design of the optical layout of the optical sensing system and its system implementation with an electronic controller. An input waveguide 871 is provided to direct light in a first propagation mode, e.g., the mode 001, from the broadband light source 201 to a light director 810. The waveguide 871 may be a mode maintaining waveguide designed to support at least one propagation mode such as the mode 001 or 002. When light is coupled into the waveguide 871 in a particular mode such as the mode 001, the waveguide 871 essentially maintains the light in the mode 001. A polarization maintaining fiber supporting two orthogonal linear polarization modes, for example, may be used as the waveguide 871. Dual-mode waveguides 272 and 273 are used to direct the light. A light director 510 is used to couple the waveguides 871, 272, and 273, to convey the mode 001 from the input waveguide 871 to one of the two modes (e.g., modes 001 and 002) supported by the dual-mode waveguide 272, and to direct light in two modes from the waveguide 272 to the dual-mode waveguide 273. In the example illustrated in FIG. 8, the light director 810 couples the light in the mode 001 from the waveguide 871 into the same mode 001 in the waveguide 272. Alternatively, the light director 810 may couple the light in the mode 001 from the waveguide 871 into the different mode 002 in the waveguide 272. The dual-mode waveguide 271 is terminated at the other end by a probe head 820 which couples a portion of light to the sample 205 for sensing.

The probe head 820 is designed differently from the prove head 320 in that the probe head 830 converts part of light in the mode 001 into the other different mode 002 when the light is reflected or scattered back from the sample 205. Alternatively, if the light in the waveguide 272 that is coupled from the waveguide 871 is in the mode 002, the probe head 820 converts that part of light in the mode 002 into the other different mode 001 when the light is reflected or scattered back from the sample 205. In the illustrated example, the probe head 820 performs these functions: a) to reverse the propagation direction of a small portion of the incoming radiation in mode 001; b) to reshape the remaining radiation and transmit it to the sample 205; and c) to convert the radiation reflected from the sample 205 to an independent mode 002 supported by the dual-mode waveguide 272. Since the probe head 820 only converts part of the light into the other mode supported by the waveguide 272, the probe head 820 is a partial mode converter in this regard. Due to the operations of the probe head 820, there are two modes propagating away from the probe head 820, the mode 001 that bypasses the sample 205 and the mode 002 for light that originates from sample reflection or back scattering.

In the examples shown in FIGS. 4-8, an optical delay is introduced at the output of the common optical waveguide to perform a time-domain imaging in extracting images from the returned light by the optical probe head. The depth scan is obtained based on a Fourier-transform from the measured signals at different phase delays at different times. Alternatively, the same designs for the optical probe head and the common optical waveguide can be used to extract images from the returned light by the optical probe head based on optical frequency domain imaging (OFDI) under a swept source optical coherence tomography configuration. Under OFDI, a wavelength-swept light source is used to produce a probe beam to the optical probe head for probing the amplitude, phase, polarization and spectral properties of back scattering light from a target, e.g., a tissue. The depth scan is obtained based on a Fourier-transform from the acquired spectra. As such, the optical delay used in the time-domain technique can be eliminated. OFDI offers intrinsic signal-to-noise ratio (SNR) advantage over the time domain techniques because the interference signal can be effectively integrated through a Fourier transform enabling significant improvements in imaging speed, sensitivity and ranging depth required for in-vivo tissue imaging.

Figure 9:
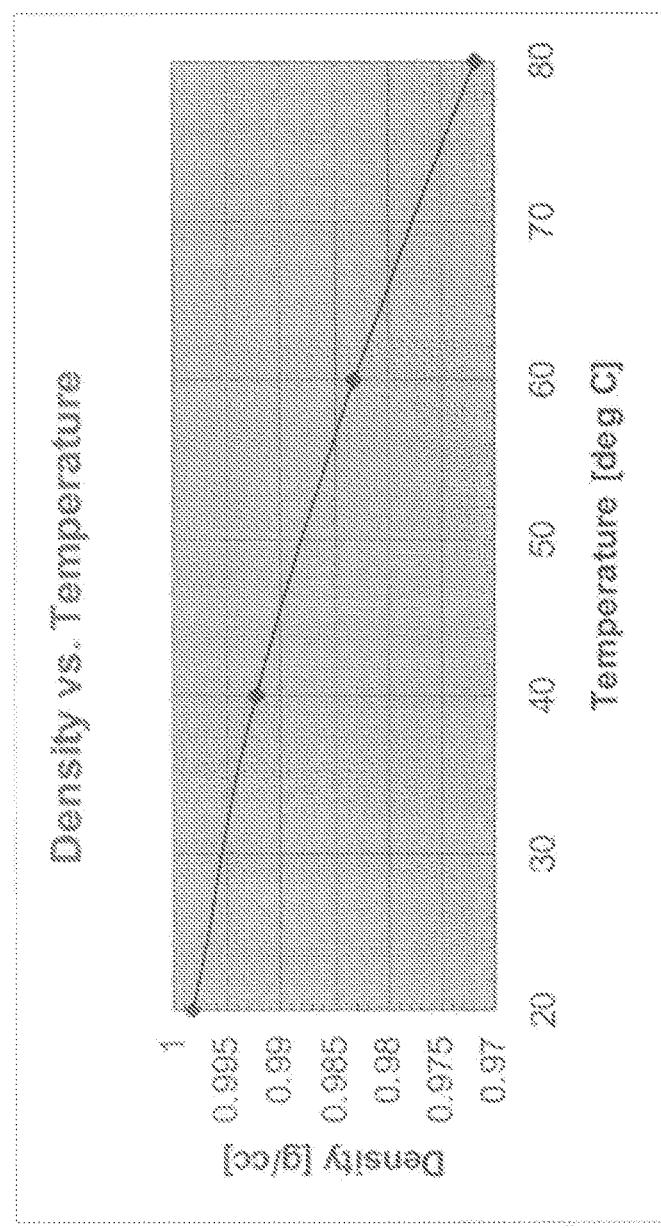
FIG. 9 shows measurements of water density and water temperature.
Figure 10:
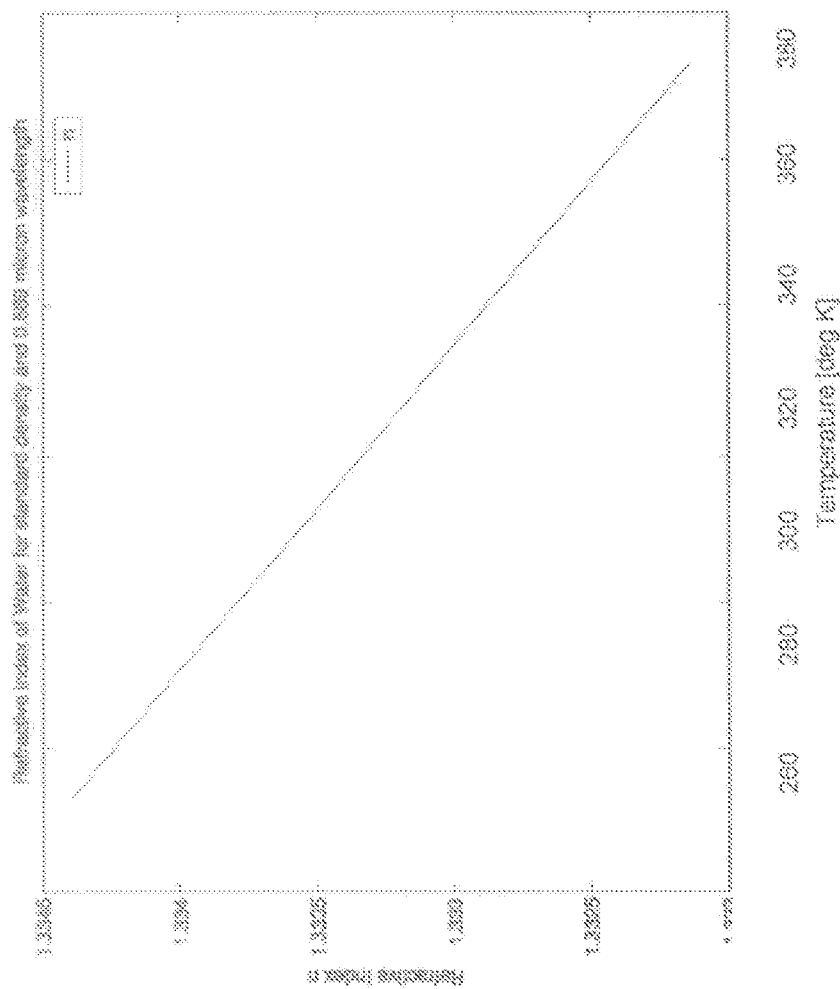
FIG. 10 shows measurements of refractive index of water and its temperature.

The optical imaging information obtained from the devices in FIGS. 4-8 based on either the time-domain imaging and frequency-domain imaging can be processed to map the thermal field or profile of a target. Changes in density, due to temperature changes, affect the optical properties [such as refractive index] of water and tissue. FIGS. 9 and 10 show measurements in water to illustrate the correlations between the temperature, density and the refractive index. FIG. 10 shows the refractive index of water as a function of temperature at standard density and 589 nm wavelength. A linear fit shows that the curve can be parameterized by $n=1.341-2.262\times10^{-5}T$.

In some implementations, the thermal treat radiation exposure is not applied to a tissue occurs during a monitoring period when the optical imaging beam is directed to the target to measure the target. In other implementations, both the optical imaging beam and the thermal treatment radiation can be applied to the target at the same time. The result of an optical index change can cause a phase shift which can lead to a full fringe for a small [1 deg. C.] temperature change allowing a two dimensional representation of the tissue density change to be assembled. The phase changes on each scanning of the relative phase between the optical imaging beam and the reflected beam that does not reach the target are translated into contrast changes. Scanning the optical imaging beam in a circumferential manner, while rapidly performing a series of imaging scans allows a raster scan image to be constructed where the thermally-induced density changes show up as contrast variations. The contrast variations reflect the combined effect of temperature changes and tissue denaturing [water loss], two important parameters for BT. By comparing the pre- and intra-BT images, the temperature increase due to thermotherapy can be extracted.

Since cytotoxicity requires only a few minutes exposure to temperatures between 50-60 deg C. and denaturation requires temperatures in excess of 60 deg C., thermally-induced image contrast is almost completely due to the change in temperature rather than water loss. However, above 60 deg C., water loss [denaturation] becomes increasingly important as an additional contribution to image contrast. The post-BT image

[after cooling] contrast will reflect changes in ASM density due to BT. Notably, the optical techniques described in this document can be used to obtain imaging of the microstructure, spectral properties and temperature profile of a target tissue, organ or object. Consequently, if we obtain a tomographic tissue image and apply an energy source [light, RF] so as to subsequently generate a temperature change [non-uniform in many cases], we can map that temperature gradient by the image contrast changes it produces. The overall functions of the present techniques include 1) monitoring therapeutic temperature ['process control'] to maintain it in the correct 'thermotherapeutic window' and 2) pre- and post-tissue imaging to assess the extent of tissue 'damage' as a result of thermotherapy.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination Only a few examples and implementations are described. One of ordinary skill in the art can readily recognize that variations, modifications and enhancements to the described examples may be made.

What is claimed is:

1. An endoscope device for providing guided thermotherapy, comprising:
   an endoscope tube comprising a hollow working channel;
   an optical catheter comprising an optical fiber located inside the hollow working channel to guide an optical probe beam and, an optical probe head, located at a distal end of the fiber, to reflect a first portion of the optical probe beam back to the fiber and to direct a section portion of the optical probe beam to a target tissue as an optical imaging beam, the optical probe head receiving light returned from the target tissue under illumination of the optical imaging beam to overlap the light returned from the target tissue with the first portion to co-propagate in the fiber away from the optical probe head;
   an optical delay device coupled to the fiber to receive the first portion and the light returned from the target tissue to produce a variable relative phase delay between the first portion and the light returned from the target tissue;
   an optical detector that detects the light of the first portion and the light returned from the target tissue from the optical delay device;
   a processing unit to receive output from the optical detector and to extract a temperature at a location illuminated by the optical imaging beam from information of the target carried by the light returned from the target tissue;
   an RF applicator engaged to the endo scope tubing and near the optical probe head to apply RF energy to the target tissue to raise a temperature at a location of the target where the RF energy is applied; and
   a control mechanism that controls an amount of the RF energy to be applied by the RF applicator to the target tissue based on the measured temperature,
   wherein the RF applicator includes a hollow tube that both conducts the RF energy for application of the RF energy to the target tissue and carries a cooling liquid or gas inside the hollow tube to cool a surface of the target to allow a temperature at a location underneath the surface to be higher than a temperature of the surface under application of the RF energy.

2. The device as in claim 1, wherein:
   the optical probe head includes a partial reflector that reflects the first portion of the optical probe beam back to the fiber and transmits the second portion of the optical probe beam as the optical imaging beam to the target tissue.

3. The device as in claim 1, wherein:
   the optical delay device includes a beam splitter to separate the light from the fiber into a first light beam along a first optical path and a second light beam along a second optical path;
   a variable optical delay element in one of the first and the second optical paths to cause the relative phase delay between the first light beam and the second light beam; and
   a beam combiner to combine the first light beam and the second light beam to produce combined light.

4. The device as in claim 1, wherein:
   the optical probe head includes a prism that reflects light to the target and collects the light returned from the target into the fiber.

5. The device as in claim 1, wherein:
   the processing unit is configured to perform a time-domain Fourier transform of the obtained signals at different relative phase delays between the first portion and the light returned from the target tissue.

6. The device as in claim 1, wherein:
   the processing unit performs a frequency-domain Fourier transform of spectra of the light from the optical probe head.

7. The device as in claim 1, comprising:
   a beam scanning mechanism to scan the optical imaging beam on the target tissue to direct the optical imaging beam to different positions on the target tissue.

8. The device as in claim 7, wherein:
   the beam scanning mechanism is configured to scan the optical imaging beam on the target tissue to enable the processing unit to obtain a two-dimensional map of temperatures at locations of the target tissue; and
   the control mechanism is configured to use the two-dimensional map of temperatures at locations of the target tissue to control the application of the RF energy to the target tissue.

9. The device as in claim 1, wherein:
   the RF applicator is structured to surround the hollow working channel; and
   a rotation mechanism engaged to the optical catheter to allow the optical catheter to rotate within the hollow working channel.

10. The device as in claim 1, wherein:
    the RF applicator comprises an expandable basket that can carry RF energy, the expandable basket structured to expand when the expandable basket is located outside a distal opening of the hollow working channel and to collapse when the expandable basket is pulled into the distal opening of the hollow working channel.

11. The device as in claim 1, wherein:
    the control mechanism is configured to control an amount of the RF energy at the target tissue to control the temperature at the target tissue between a low limit above which a thermotherapeutic effect is present and a high limit above which a damage to the target tissue occurs.

12. The device as in claim 1, wherein:

the processing unit is configured to further use the optical imaging beam to obtain an image of a location of the target tissue illuminated by the optical imaging beam, in addition to obtaining the measured temperature; and the control mechanism is configured to use both the measured temperature and the obtained image from the optical imaging beam to monitor and control application of the RF energy to the target tissue.

13. The device as in claim 1, wherein:

the processing unit is configured to detect a change in an optical interference between the first portion of the optical probe beam that is directed back to the fiber and does not reach the target tissue, and the light returned from the target tissue caused by the application of the RF energy to the target tissue to measure a change in density of the target tissue; and the processing unit is further configured to use the measured change in density of the target tissue to obtain the measured temperature.

14. The device as in claim 13, wherein:

the processing unit is configured to perform a frequency-domain Fourier transform of spectra of light in the fiber that combines the light returned from the target tissue and the first portion of the optical probe beam that is directed back to the fiber and does not reach the target tissue to extract a change to the optical interference caused by the application of the RF energy to the target tissue and to measure a change in density of the target tissue.

15. The device as in claim 1, wherein:

the processing unit is configured to obtain image contrasts from the light returned from the target tissue before and after the application of the RF energy, compare the obtained image contrasts from the light returned from the target tissue before and after the application of the RF energy to obtain a contrast variation caused by application of the RF energy, and use the contrast variation to obtain the measured temperature.

* * * * *